(12) United States Patent
Tanaka et al.

(10) Patent No.: US 7,871,638 B2
(45) Date of Patent: Jan. 18, 2011

(54) COMPOSITE MATERIAL CONTAINING A CALCIUM PHOSPHATE GRADIENT

(75) Inventors: Junzo Tanaka, Ibaraki (JP); Tetsushi Taguchi, Ibaraki (JP)

(73) Assignees: Japan Science and Technology Agency, Kawaguchi-shi (JP); National Institute for Materials Science, Tsukuba-shi (JP)

( * ) Notice: Subject to any disclaimer, the term of this patent is extended or adjusted under 35 U.S.C. 154(b) by 701 days.

(21) Appl. No.: 10/516,818

(22) PCT Filed: May 2, 2003

(86) PCT No.: PCT/JP03/05611

§ 371 (c)(1), (2), (4) Date: Dec. 7, 2004

(87) PCT Pub. No.: WO03/103740

PCT Pub. Date: Dec. 18, 2003

(65) Prior Publication Data

US 2006/0165663 A1 Jul. 27, 2006

(30) Foreign Application Priority Data

Jun. 10, 2002 (JP) .............................. 2002-168588

(51) Int. Cl.
- *A61F 2/00* (2006.01)
- *C12N 11/14* (2006.01)
- *C12N 11/04* (2006.01)
- *C12N 5/00* (2006.01)

(52) U.S. Cl. ...................... 424/423; 435/176; 435/182; 435/395

(58) Field of Classification Search ........................ None
See application file for complete search history.

(56) References Cited

U.S. PATENT DOCUMENTS

| | | | | |
|---|---|---|---|---|
| 4,947,840 A | * | 8/1990 | Yannas et al. | ................. 602/50 |
| 6,387,414 B1 | * | 5/2002 | Akashi et al. | ................ 424/602 |
| 6,454,811 B1 | * | 9/2002 | Sherwood et al. | ........ 623/23.76 |
| 6,969,523 B1 | * | 11/2005 | Mattern et al. | .............. 424/423 |

FOREIGN PATENT DOCUMENTS

| | | |
|---|---|---|
| EP | 1 230 938 A1 | 8/2002 |
| JP | 10-52485 | 2/1998 |
| WO | WO 01/36012 A1 | 5/2001 |

OTHER PUBLICATIONS

Taguchi et al., Biomaterials, vol. 22, Issue 1, Jan. 2001, pp. 53-58.*
Junzo Tanaka et al.; Journal of Japanese Society for Biomaterial, vol. 20, No. 2, pp. 77 to 84, 2002. Cited in the int'l. search report.
Junzo Tanaka, Tetsushi Taguchi, Journal of Japanese Society for Biomaterials, 2002, Vol. 20, No. 2, pp. 77 to 84, full text.
International Search Report dated May 29, 2003, issued in corresponding International Application No. PCT/JP03/05611.

* cited by examiner

*Primary Examiner*—David M Naff
(74) *Attorney, Agent, or Firm*—Westerman, Hattori, Daniels & Adrian, LLP

(57) ABSTRACT

This invention relates to a scaffold consisting of a biodegradable polymeric material with a composition gradient of calcium phosphate that is capable of effectively regenerating the hard/soft tissue interface and an implant for hard/soft tissue filling with the utilization of such scaffold.

7 Claims, 7 Drawing Sheets
(4 of 7 Drawing Sheet(s) Filed in Color)

COMPOSITE MATERIAL CONTAINING A CALCIUM PHOSPHATE GRADIENT

TECHNICAL FIELD

The present invention relates to a scaffold for regenerating a hard/soft tissue interface. More particularly, the present invention relates to a scaffold consisting of a biodegradable polymeric material with a composition gradient of calcium phosphate that is capable of effectively regenerating the interface between hard tissue (bone or tooth) and soft tissue (tissue other than bone or tooth). Further, the present invention relates to an implant for hard/soft tissue filling with the utilization of such scaffold.

BACKGROUND ART

Cartilage is soft tissue with a limited capacity for regeneration. Thus, it is difficult to naturally regenerate cartilage that has been fractured or defected due to accidents, diseases, or the like. In the past, accordingly, cartilage defects used to be mainly restored by a technique referred to as "mosaicplasty," in which cartilage tissues were harvested from a non-weight-bearing region and transplanted into the affected area. Use of a patient's own tissues, however, imposes a heavy burden on the patient, and the amounts thereof that can be obtained are limited. Accordingly, the allograft technique that utilizes cartilage tissues of another individual has been attempted as an alternative thereto. Because of the problems of immunological rejection or infection, sufficient outcomes have not yet been attained.

Research into regenerative medicine has recently been making progress. In such regenerative medicine, cells removed from a body are cultured and organized in vitro, tissues that are as similar as possible to those in the body are reconstructed, and they are used to replace tissues in the body. Since the tissues regenerated in such a technique originate from the patient, they do not cause problems such as immunological rejection or infection. Thus, this technique has drawn attention as an ideal means for restoring tissue defects. Due to the reasons as mentioned above, regeneration of cartilage tissues in vitro has been attempted by many research institutes.

Cells exist in a body by adhering to the extracellular matrix and differentiate and proliferate with the use thereof as a scaffold. In order to construct a perfect three-dimensional tissue via in vitro cell culture, accordingly, it is necessary to provide a scaffold that is suitable for cell differentiation and proliferation. Up to the present, beneficial outcomes of tissue regeneration have been attained in hard tissue regeneration with the use of collagen, agarose, or other types of gel for a scaffold.

Even when the regenerated cartilage tissues are transplanted in the body, a new issue arises. That is, cartilage defects cannot be sufficiently supplemented due to weak adhesion between the bone tissues at the transplantation site and the regenerated cartilage tissues.

Schaefer et al. reported a method for preparing hard/soft tissue interface-like tissues by constructing cartilage-like tissues with the use of a biodegradable scaffold consisting of polyglycolic acid, separately constructing bone-like tissues with the use of a scaffold consisting of a lactic acid-glycolic acid copolymer and polyethylene glycol, and then artificially bonding them (Schaefer et al., Biomaterials 21, 2000, pp. 2599-2606). Hard/soft tissue interface-like tissues (bone/cartilage interface-like tissues) prepared by such method, however, are disadvantageously insufficient in terms of forming a bond between hard tissue (bone) and soft tissue (cartilage).

In contrast, Yaylaoglu et al. reported a method for preparing a bone/cartilage implant by generating calcium phosphate in a lyophilized collagen sponge (Gelfix® membrane, Abdi-Ibrahim), and culturing cartilage cells using it as a scaffold (Yaylaglu et al., Biomaterials 20, 1999, pp. 1513-1520). A material that simply comprises calcium phosphate, however, insufficiently bonds to hard tissues (bones) and thus cannot effectively regenerate a hard/soft tissue interface (a bone/cartilage interface herein).

DISCLOSURE OF THE INVENTION

Objects of the present invention are to provide a scaffold that effectively regenerates a hard/soft tissue interface and to provide an implant that can sufficiently supplement hard tissue/soft tissue defects with the utilization of such scaffold.

The present inventors have conducted concentrated studies in order to attain the above objects. Consequently, they considered that a hard tissue-soft tissue bond could be improved by forming an apatite structure similar to a hard tissue structure on the contact surface therebetween. They also found that a scaffold that sufficiently adheres to hard tissues and has excellent capacity of regenerating soft tissues could be obtained by generating a composition gradient of calcium phosphate in a biodegradable polymeric material via alternate soaking. This has led to the completion of the present invention.

Specifically, the present invention provides the following (1) to (8).

(1) A composite material with a composition gradient of calcium phosphate in a biodegradable polymeric material.

(2) The composite material according to (1), wherein the biodegradable polymeric material is at least one member selected from among glycosaminoglycan, collagen, and a composite thereof.

(3) The composite material according to (1), wherein the biodegradable polymeric material is a crosslinked product of glycosaminoglycan and collagen.

(4) A scaffold for cell differentiation and proliferation consisting of the composite material according to any of (1) to (3).

(5) The scaffold according to (4), which can effectively regenerate a hard/soft tissue interface.

(6) An implant for hard/soft tissue filling comprising the composite material according to any of (1) to (3).

(7) The implant according to (6), which further comprises cells.

(8) A method for producing a composite material with a composition gradient of calcium phosphate in a biodegradable polymeric material by alternately soaking one side or part of the biodegradable polymeric material in a calcium ion-containing solution and the same side or part in a phosphate ion-containing solution.

Hereafter, the present invention is described in detail.

1. Composite Material with a Composition Gradient of Calcium Phosphate

The present invention relates to a composite material with a composition gradient of calcium phosphate in a biodegradable polymeric material.

1.1 Biodegradable Polymeric Material

A biodegradable polymeric material constituting the composite material according to the present invention is a polymeric material that is degraded and absorbed in a body.

Examples thereof include glycosaminoglycan such as hyaluronic acid, chondroitin, chondroitin sulfate, dermatan sulfate, heparin, heparan sulfate, or keratan sulfate and a chemically modified composite thereof, collagen, polylactic acid, polyglycolic acid, polyethylene glycol, and a copolymer or crosslinked product thereof, and a composite of two or more of the aforementioned materials.

In the present invention, glycosaminoglycan such as hyaluronic acid, chondroitin sulfate, keratan sulfate, heparin, or heparan sulfate, collagen, or a composite of two or more thereof, which is a constituent of soft tissues such as a cartilage matrix, is preferably used as a biodegradable polymeric material. The aforementioned composite may be prepared by simply mixing two or more kinds of biodegradable polymeric materials and then dehydrating and molding the mixture. Preparation of a composite by adequately crosslinking biodegradable polymeric materials with each other is preferable because the strength of the biodegradable polymeric material and the absorption rate in vivo are enhanced. A preferable example of the biodegradable polymeric material that is used in the present invention is a composite of hyaluronic acid and type II collagen.

The origin of the hyaluronic acid is not particularly limited. Hyaluronic acid may be extracted from crista galli, umbilical cord, or other substances. It may be produced by a microorganism. The molecular weight of hyaluronic acid is not particularly limited, and it is preferably about 100,000 to 1,000,000.

The origin of collagen that is used for the biodegradable polymeric material according to the present invention is not particularly limited. Examples thereof include collagen obtained from tissues of mammalians (such as cows, pigs, horses, rabbits, or mice), birds (such as chickens), and fish. Alternatively, collagen may be obtained by a gene recombination technique.

At present, 19 different species of collagens are known to be present, and any of these collagens may be employed. When collagen is used for the purpose of regenerating a bone/cartilage interface, a main component of a cartilage matrix, i.e., type II collagen, is particularly preferable.

The majority of the forms of naturally-occurring collagen are insoluble. Thus, use of soluble collagen, which is prepared by treating such insoluble collagen with alkali or enzymes, is preferable in the following respects. That is, soluble collagen is easy to use, and antigenic portions are removed therefrom. Phthalated collagen is preferable since it is dissolved in a buffer of any pH level and is easy to use.

1.2 Calcium Phosphate

Calcium phosphate, which constitutes the composite material according to the present invention, is a group of compounds represented by a chemical formula such as $CaHPO_4$, $Ca_3(PO_4)_2$, $Ca_4O(PO_4)_2$, $Ca_{10}(PO_4)_6(OH)_2$, $CaP_4O_{11}$, $Ca(PO_3)_2$, $Ca_2P_2O_7$, or $Ca(H_2PO_4)_2 \cdot H_2O$. If such calcium phosphate is soaked in an aqueous solution, it is converted to thermodynamically stable hydroxyapatite in a composite.

Hydroxyapatite is a compound generally represented by the formula $Ca_5(PO_4)_3OH$ and is a major component of hard tissues (bone or tooth) of a mammalian in addition to collagen. Hydroxyapatite comprises the aforementioned group of calcium phosphates, and the $PO_4$ and OH components of apatite in hard tissues of an organism are often substituted with $CO_3$ in the atmosphere. The composite material according to the present invention may comprise such substitution to some extent (about 0% to 10% by mass).

1.3 Composition Gradient of Calcium Phosphate

The composite material according to the present invention has a composition gradient of calcium phosphate in a biodegradable polymeric material. The term "gradient" used herein refers to changes with a constant gradient. Specifically, the biodegradable polymeric material comprises calcium phosphate from one side toward the other with an increasing linear gradient.

2. Method for Preparing Composite Material with a Composition Gradient of Calcium Phosphate 2.1 Preparation of Biodegradable Polymeric Material As a preferable embodiment of a biodegradable polymeric material that is used in the composite material according to the present invention, a method for preparing a crosslinked product of hyaluronic acid and type II collagen is described.

Hyaluronic acid in amounts of 0.1% to 50% relative to collagen is dissolved in a physiological buffer such as a 0.01 M to 0.5 M phosphate buffer, and the resultant is added to an adequate amount of collagen. A crosslinking agent (or a condensing agent) is then added thereto to introduce chemical crosslinking. Examples of crosslinking agents that can be used include: aldehyde crosslinking agents such as glutaraldehyde or formaldehyde; isocyanate crosslinking agents such as hexamethylene diisocyanate; carbodiimide crosslinking agents such as 1-ethyl-3-(3-dimethylaminopropyl)carbodiimide hydrochloride; polyepoxy crosslinking agents such as ethylene glycol diethyl ether; and transglutaminase. In the present invention, a tetrafunctional crosslinking agent, pentaerythritol polyethylene glycol ether tetrasuccinimidyl glutarate (PTE-10TGS), is preferable. The concentration of a crosslinking agent to be used is suitably determined in accordance with a composition or amount of a substance to be crosslinked. In the case of PTE-10TGS, a crosslinking agent is preferably added to a reaction solution to bring the final concentration thereof in the reaction solution to about 0.1 mM to 10 mM.

In addition to the aforementioned chemical crosslinking, crosslinking may be introduced via physical crosslinking using γ rays, ultraviolet rays, thermal dehydration, an electron beam, or the like.

Any functional groups of collagen and hyaluronic acid may be crosslinked. Crosslinking may be introduced not only between collagen and hyaluronic acid but also between collagen molecules or between hyaluronic acid molecules. Crosslinking between a hydroxyl group and a ϵ-amino group and between ϵ-amino groups in the aforementioned molecules is particularly preferable.

2.2 Composition Gradient of Calcium Phosphate (Formation of Hydroxyapatite)

A composition gradient of calcium phosphate in a biodegradable polymeric material is attained via alternate soaking. For example, one side of a biodegradable polymeric material is soaked in a phosphate ion- or calcium ion-containing solution.

Examples of phosphagens for a phosphate ion-containing solution that are used herein include disodium hydrogenphosphate, sodium dihydrogen phosphate, dipotassium hydrogen phosphate, potassium dihydrogen phosphate, and phosphoric acid. The concentration of the phosphate ion-containing solution is preferably between 0.1 mM and 500 mM.

Examples of calcium sources for a calcium ion-containing solution that are used herein include calcium chloride, calcium carbonate, calcium acetate, and calcium hydroxide. The concentration of the calcium ion-containing solution is preferably between 0.1 mM and 800 mM. This calcium ion-containing solution may be a suspension as long as it is homogenous.

In the present invention, one side of a biodegradable polymeric material is soaked in a phosphate ion-containing solution and the same side is soaked in a calcium ion-containing solution in order to make the biodegradable polymeric material with a composition gradient of calcium phosphate. Preferably, the biodegradable polymeric material is soaked in a solution for 10 seconds to 120 minutes, and such soaking is repeated more than once. Thus, the majority of the calcium phosphate in the biodegradable polymeric material forms an apatite structure.

2.3 Confirmation of a Composition Gradient of Calcium Phosphate

The distribution of calcium phosphates in the composite material that was prepared by the method described in the section above can be confirmed by a variety of analysis techniques. Examples thereof are X-ray diffraction, microscopy, infrared absorption spectrum, and elementary analysis. These techniques can be carried out solely or in combinations of two or more.

3. Scaffold for Regenerating Hard/Soft Tissue Interface, Implant for Hard/Soft Tissue Filling 3.1 Scaffold for Regenerating Hard/Soft Tissue Interface The composite material according to the present invention comprises a biodegradable polymeric material as the matrix and thus can be used to construct soft tissues in vitro and in vivo for a suitable scaffold for cell culturing.

The biodegradable polymeric material with a composition gradient of calcium phosphate, and the crystallinity of the calcium phosphate formed is low. Accordingly, the biocompatibility thereof is high. Unlike conventional scaffolds, the composite material according to the present invention is highly compatible with hard tissues (bones or teeth) at a site with a high hydroxyapatite density. Therefore, the composite material according to the present invention can regenerate the hard/soft tissue interface.

The composite material according to the present invention can be adequately used as a scaffold for regenerating a hard/soft tissue interface. In the present invention, the term "hard tissue" refers to tissue forming a hard intercellular substance, such as bone or tooth. The term "soft tissue" refers to tissues other than hard tissues (such as cartilage).

3.2 Implant for Hard/Soft Tissue Filling

Further, if cells are inoculated (after being cultured in vitro or directly without culturing) to the composite material according to the present invention and transplanted to hard tissue/soft tissue defects, the resultant can be preferably used as an implant for filling hard tissue/soft tissue defects. While tissue regeneration makes progress with the aid of the inoculated cells using the transplanted composite material as a scaffold, the composite material is gradually absorbed and substituted with the regenerated soft tissues at the final stage.

When regeneration of a bone/cartilage interface is intended, examples of such cells that can be adequately used include cartilage cells, osteoblasts, mesenchymal stem cells, and ES cells. Hyaluronic acid or collagen, i.e., a constituent of a biological cartilage matrix, can be used as a biodegradable polymeric material, and this can be a scaffold that is suitable for cell differentiation and proliferation as described above.

3.3 Others

The configurations and shapes of the scaffold and those of the implant for hard/soft tissue filling according to the present invention are not particularly limited. They can take any desired configurations or shapes, such as sponges, meshes, unwoven fabric products, discs, films, sticks, particles, or pastes. These configurations and shapes may be suitably selected depending on their applications.

The scaffold and the implant for hard/soft tissue filling according to the present invention can suitably contain other components within the scope of the present invention. Examples of such components include: growth factors such as basic fibroblast growth factors (bFGF), platelet-derived growth factors (PDGF), insulin and insulin-like growth factors (IGF), hepatocyte growth factors (HGF), glial-derived neurotrophic factors (GDNF), neurotrophic factors (NF), transforming growth factors (TGF), and vascular endothelial growth factors (VEGF); other types of cytokines such as bone morphogenetic factors (BMP) and transcription factors; hormones; inorganic salts such as St, Mg, Ca, and $CO_3$; organic substances such as citric acid and phospholipids; and drugs such as antitumor agents.

The composite material according to the present invention is highly compatible with a hard tissue. Accordingly, it can be an ideal scaffold for regenerating a hard/soft tissue interface or an ideal implant for hard/soft tissue filling.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

This description includes a part or all of the contents as disclosed in the description of Japanese Patent Application No. 2002-168588, which is a priority document of the present application.

BEST MODES FOR CARRYING OUT THE INVENTION

The present invention is hereafter described in more detail with reference to the examples, although the technical scope of the present invention is not limited thereto.

Example 1

Preparation of Composite Material with a Composition Gradient of Calcium Phosphate 1. Testing Method 1.1 Preparation of Cartilage Matrix Among the main cartilage components, i.e., type II collagen (Col), hyaluronic acid (HyA), and chondroitin sulfate (ChS), type II collagen (bovine-derived, Nitta Gelatin Inc.) and hyaluronic acid (molecular weight of 640,000, Seikagaku Corporation) were subjected to the experiment.

The prepared cartilage matrices are shown below.

1) Collagen (Col/Hya0): the final concentration of collagen was 1%.

2) Collagen+2% by weight hyaluronic acid (Col/HyA2): the final concentration of 2% by weight hyaluronic acid-containing collagen was 1%.

3) Collagen+10% by weight hyaluronic acid (Col/HyA10): the final concentration of 10% by weight hyaluronic acid-containing collagen was 1%.

Pentaerythritol polyethylene glycol ether tetrasuccinimidyl glutarate (PTE-10TGS) was used as a crosslinking agent, and the crosslinking agent was added to a final concentration of 0.3 mM or 1.0 mM. As a solvent, a 0.1 M phosphate buffer solution (PBS) at a pH level of 7.4 was used.

1.2 Formation of Hydroxyapatite (Alternate Soaking)

Figure 1:
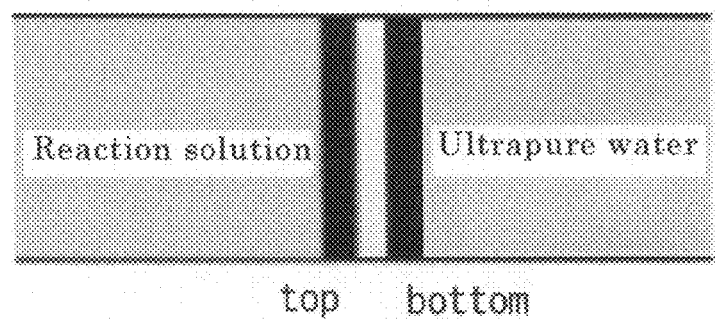
FIG. 1 shows an apparatus for preparing the scaffold according to the present invention.

As shown in FIG. 1, the prepared cartilage matrix was sandwiched between doughnut-shaped rubbers and inserted in a syringe. One side of the matrix was treated with a reaction solution, and the other side thereof was treated with ultrapure water.

As the reaction solution, $CaCl_2$/Tris-HCl and $Na_2HPO_4$ were used.

A $CaCl_2$/Tris-HCl solution (pH 7.4) was placed in the reaction solution side, and the cartilage matrix was allowed to stand at 37° C. for 5 minutes. Thereafter, the cartilage matrix was washed with ultrapure water, the reaction solution was exchanged with $Na_2HPO_4$, and the cartilage matrix was allowed to stand in the same manner at 37° C. for 5 minutes. This procedural cycle was repeated 30 times.

1.3 Analysis of Samples

Samples after each cycle were independently subjected to substance identification via X-ray diffraction and Fourier Transform InfraRed (FT-IR) spectrometry, scanning electron microscopy (SEM), and elementary analysis. Inorganic components were subjected to quantitative analysis via differential scanning calorimetry.

2. Test Results 2.1 Observation Under Stereoscopic Microscope

Figure 2:
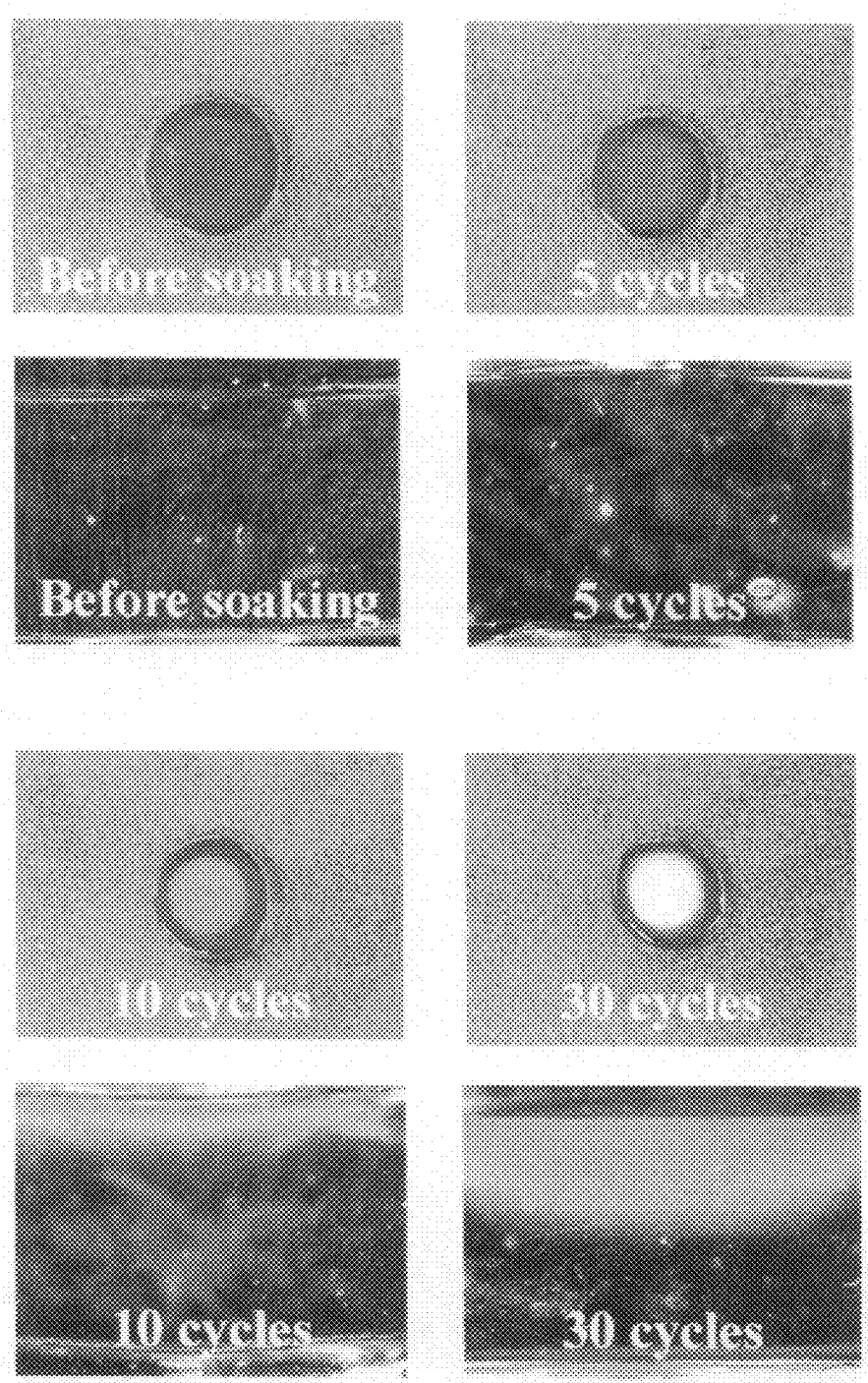
FIG. 2 is a photograph showing a cross-section of the prepared scaffold observed under a stereoscopic microscope.

White crystals formed a deposit on the cartilage matrix as the number of cycles increased. The cross-section of the cartilage matrix was observed under a stereoscopic microscope (VH-7000C, Keyence, magnification: ×35), and gradient formation of crystals was observed inwardly from one side of the matrix (the reaction side) (FIG. 2).

2.2 Elementary Analysis of Cross-Section

Figure 3:
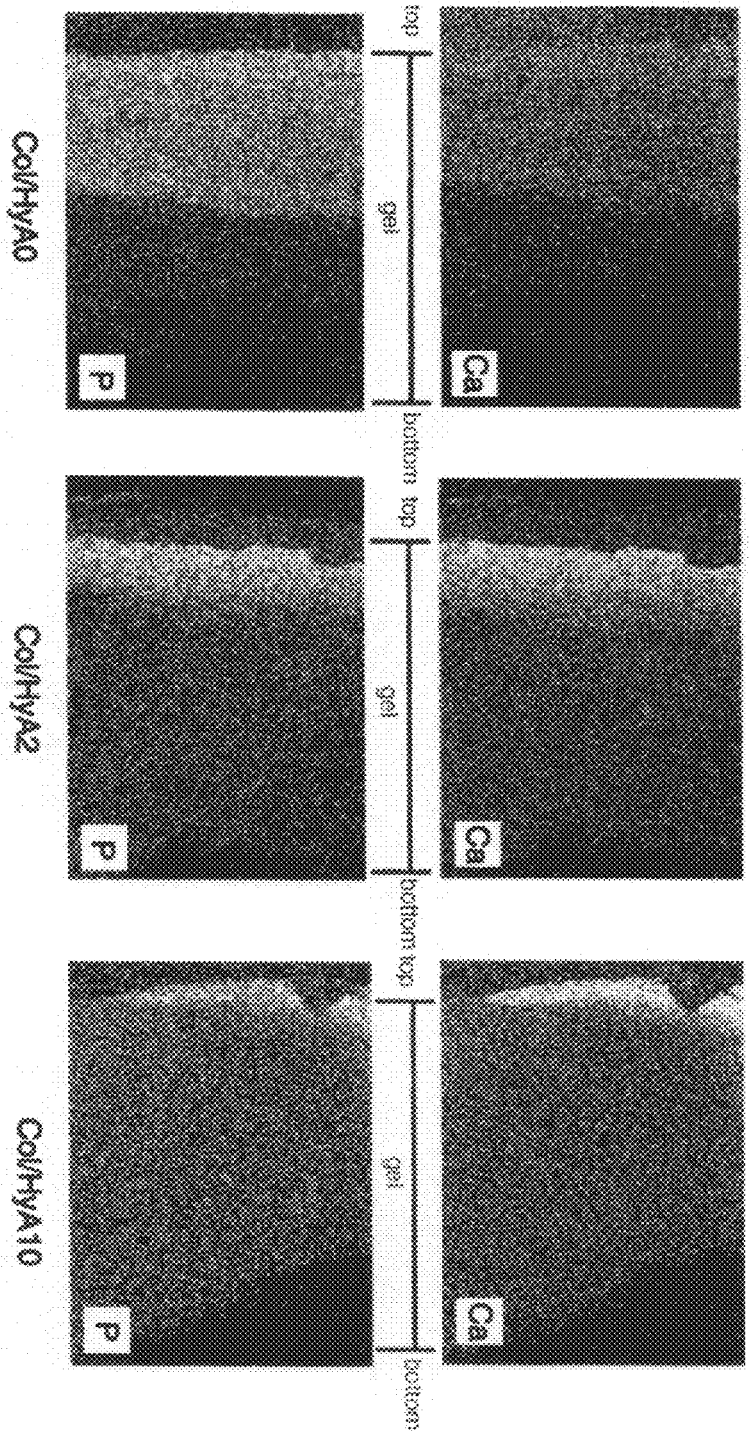
FIG. 3 shows the results of elementary analysis of a cross-section of the prepared scaffold.

The alternately soaked cartilage matrix was lyophilized, and the cross-section thereof was subjected to elementary analysis. A large quantity of Ca and P were distributed on the reaction surface (the top side), and the density thereof became smaller toward the other side of the matrix. Thus, gradient formation of crystals in the matrix was confirmed (FIG. 3).

2.3 X-Ray Diffraction

Figure 4:
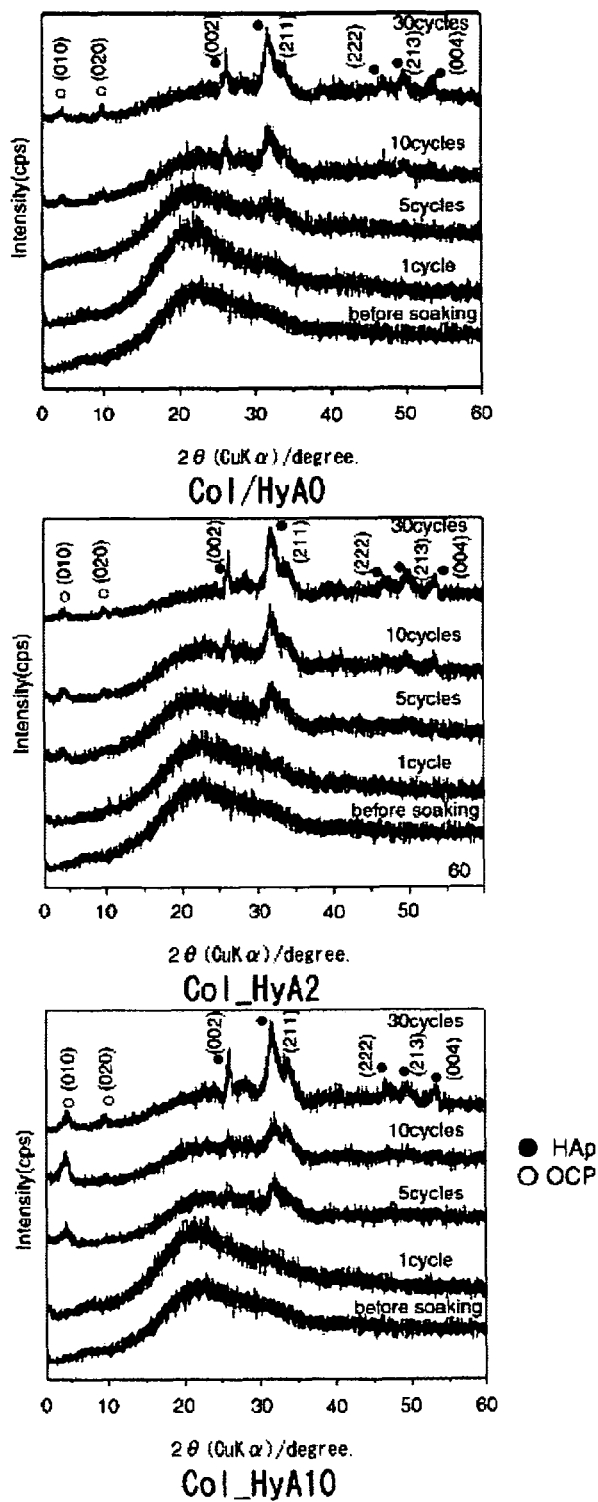
FIG. 4 is a graph showing the results of X-ray diffraction of the prepared scaffold (A: Col/HyA0; B: Col/HyA2; C: Col/HyA10).

Samples after each reaction cycle were subjected to X-ray diffraction analysis using PW1729 (Philips), and the formed white crystals were identified (FIG. 4). An intense peak of hydroxyapatite (HAp) was observed at around 30 degrees, and the line of maximum intensity of octacalcium phosphate (OCP) was observed at around 4 degrees. The peak intensity increased as the number of cycles increased. No difference was observed in white crystals among cartilage matrices.

Figure 5:
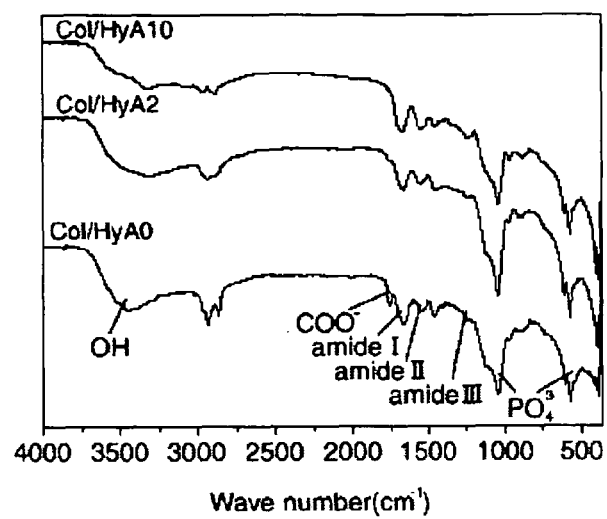
FIG. 5 is a graph showing the infrared absorption spectrum of the prepared scaffold.
Figure 5:
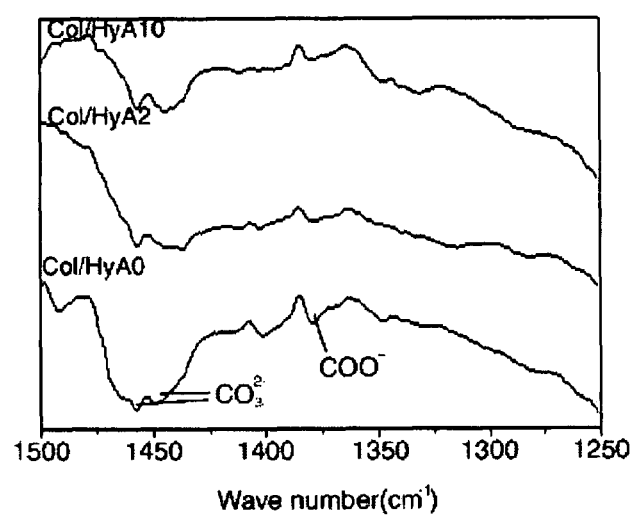

2.4 Identification of Calcium Phosphate Via Fourier Transform Infrared (Ft-IR) Spectrometry FT-IR spectrometry was carried out via the diffuse reflection method using Spectrum 2000 (Perkin Elmers). Portions where each sample after the 30th cycle had been alternately soaked (portions where calcium phosphate was generated) were selectively removed from the gel, and the removed gel portions were lyophilized, followed by identification based on FT-IR (FIG. 5).

In the case of Col/HyA0, oscillations were observed at 1744.39 $cm^{-1}$ ($COO^-$), 1228.80 $cm^{-1}$ (amide III), 1539.99 $cm^{-1}$ (amide II), 1653.45 $cm^{-1}$ (amide I), and 1378.23 $cm^{-1}$ ($COO^-$). In the case of Hap, oscillations were observed at 3437.50 $cm^{-1}$ and 1447.75 $cm^{-1}$ (OH), 1456.82 $cm^{-1}$ ($CO_3^{2-}$), and 1033 $cm^{-1}$, 600.51 $cm^{-1}$, and 561.92 $cm^{-1}$ ($PO_4^{3-}$).

In the case of Col/HyA2, oscillations were observed at 1232.59 $cm^{-1}$ (amide III), 1540.23 $cm^{-1}$ (amide II), 1651.88 $cm^{-1}$ (amide I), and 1379.07 $cm^{-1}$ ($COO^-$). In the case of Hap, oscillations were observed at 3304.81 $cm^{-1}$ (OH), 1456.09 $cm^{-1}$ and 1443.09 $cm^{-1}$ ($CO_3^{2-}$), and 1038 $cm^{-1}$, 600.90 $cm^{-1}$, and 562.89 $cm^{-1}$ ($PO_4^{3-}$).

In the case of Col/HyA10, oscillations were observed at 1231.94 $cm^{-1}$ (amide III), 1530.04 $cm^{-1}$ (amide II), 1662.34 $cm^{-1}$ (amide I), and 1379.47 $cm^{-1}$ ($COO^-$). In the case of Hap, oscillations were observed at 3306.22 $cm^{-1}$ (OH), 1456.39 $cm^{-1}$ and 1443.62 $cm^{-1}$ ($CO_3^{2-}$), and 1038 $cm^{-1}$, 600.88 $cm^{-1}$, and 563.04 $cm^{-1}$ ($PO_4^{3-}$).

Figure 6:
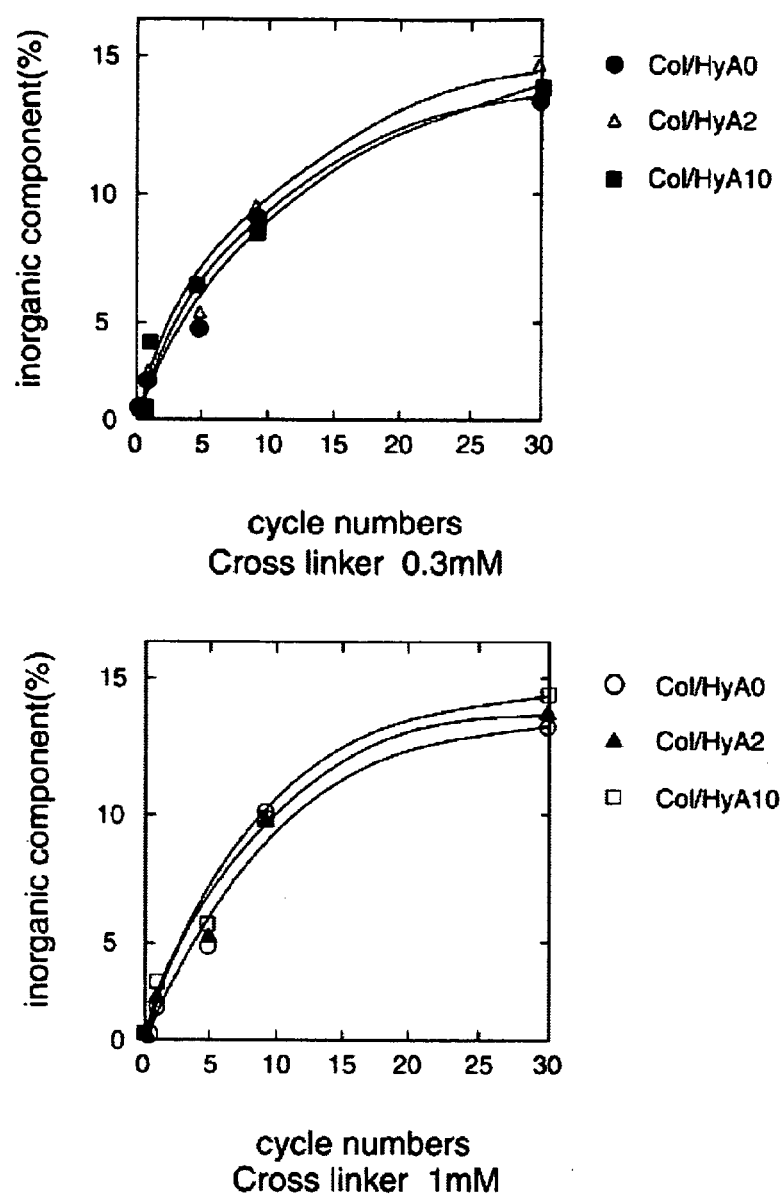
FIG. 6 is a graph showing the results of quantitative analysis of inorganic components via differential scanning calorimetry.

2.5 Quantitative Analysis of Inorganic Component Via Differential Scanning Calorimetry The lyophilized cartilage matrix was subjected to differential scanning calorimetry using a Thermo Plus TG8120 (Rigaku), organic components were removed, and the amounts (%) of the remaining inorganic components were calculated (FIG. 6). The amounts of inorganic components increased as the number of cycles increased. Concentration dependence was not observed in hyaluronic acid. With the concentration range of the crosslinking agent that had been employed, no difference was observed in the amounts of inorganic components.

2.6 Electron Microscopy

Figure 7:
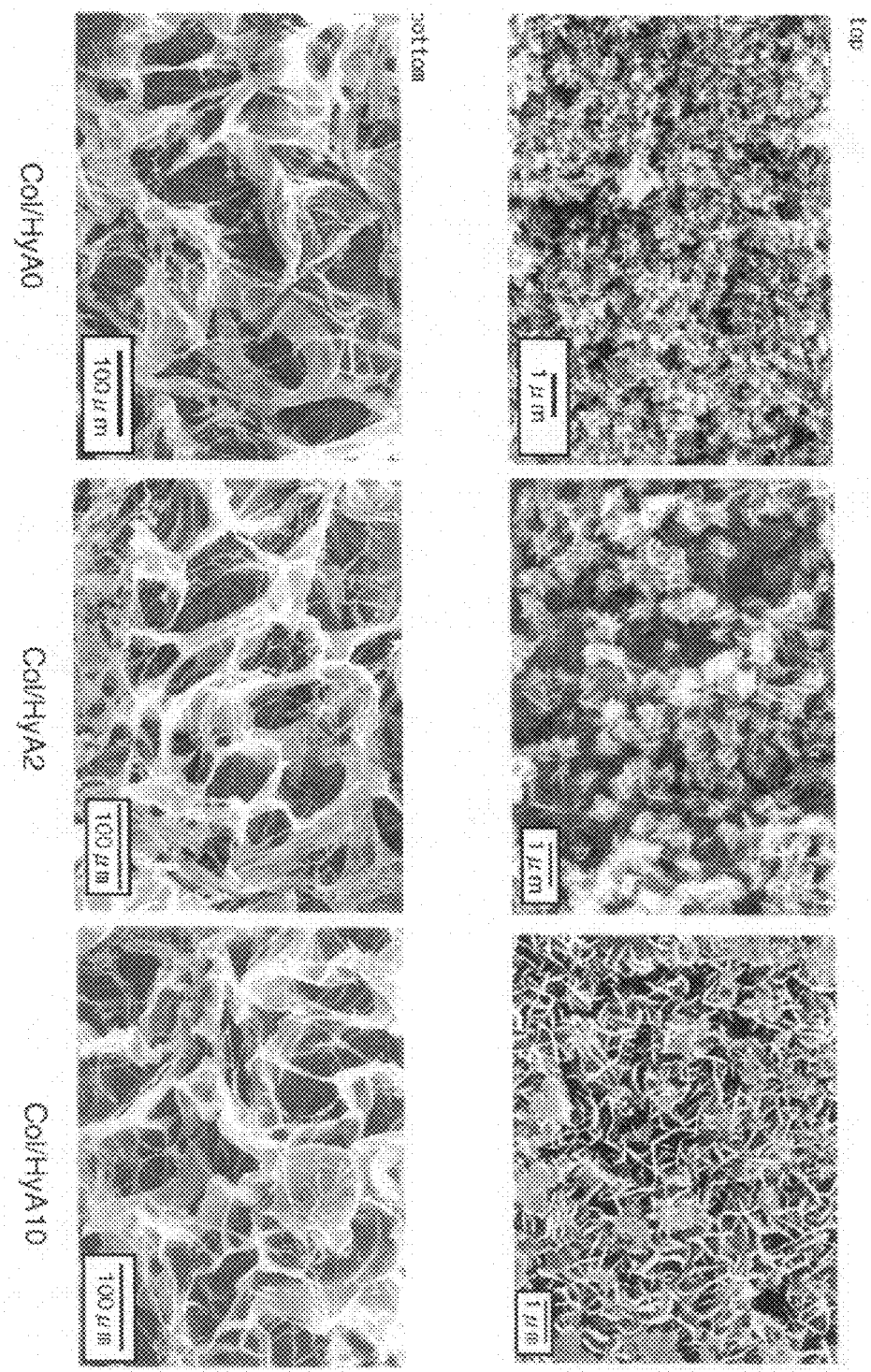
FIG. 7 is an image showing the results of surface observation under an electron microscope.

The reaction surface (top) and the no-reaction surface (bottom) were observed under a scanning electron microscope (JSM-5600LV, JEOL, magnification: ×10,000 (for the reaction surface) and ×200 (for the no-reaction surface)) (FIG. 7). Scale-like substances were observed on the reaction surface. There were sponge-like pores that were large enough for cells to enter therein (50 μm to 200 μm) on the no-reaction surface.

All publications, patents, and patent applications cited herein are incorporated herein by reference in their entirety.

INDUSTRIAL APPLICABILITY

The present invention provides a biodegradable polymeric material with a composition gradient of calcium phosphate.

The biodegradable polymeric material sufficiently adheres to hard tissues and can serve as an excellent scaffold for cell differentiation and proliferation of soft tissues. More specifically, such material can be utilized as a scaffold for regenerating a hard/soft tissue interface or as an implant for hard/soft tissue filling.

The invention claimed is:

1. A composite material, comprising:
a biodegradable polymeric material, and
calcium phosphate in the biodegradable polymeric material,
wherein the calcium phosphate is contained in the biodegradable polymeric material in a gradient of calcium phosphate that varies in the biodegradable polymeric material from a first side of said biodegradable polymeric material to an opposite second side of said biodegradable polymeric material with an increasing linear gradient,
wherein the biodegradable polymeric material is selected from the group consisting of glycosaminoglycan, collagen, and a composite of glycosaminoglycan and collagen, and
wherein said gradient of calcium phosphate is formed by alternately soaking the opposite second side of the biodegradable polymeric material in a calcium ion-containing solution and the opposite second side of the biodegradable polymeric material in a phosphate ion-containing solution.

2. The composite material according to claim 1, wherein the biodegradable polymeric material is a crosslinked product of glycosaminoglycan and collagen.

3. A scaffold for cell differentiation and proliferation, comprising:
the composite material according to claim 1,
wherein the gradient of calcium phosphate is a constant gradient.

4. A scaffold for cell differentiation and proliferation, comprising:
the composite material according to claim 1, and
one or more components selected from the group consisting of basic fibroblast growth factors (bFGF), vascular endothelial growth factors (VEGF), bone morphogenetic factors (BMP), and inorganic salts comprising calcium salt.

5. The scaffold according to claim 4, which further comprises cells.

6. The scaffold according to claim 4, wherein the scaffold is porous.

7. A method for producing a composite material, comprising:
providing a biodegradable polymeric material selected from the group consisting of glycosaminoglycan, collagen, and a composite of glycosaminoglycan and collagen, said biodegradable polymeric material having a first side and an opposite second side, and
alternately soaking the opposite second side of the biodegradable polymeric material in a calcium ion-containing solution and the opposite second side of the biodegradable polymeric material in a phosphate ion-containing solution, whereby a gradient of calcium phosphate is formed that varies in the biodegradable polymeric material from the first side of said biodegradable polymeric material to the opposite second side of the biodegradable polymeric material with an increasing linear gradient.

* * * * *